US006207182B1

(12) United States Patent
Raimondi

(10) Patent No.: US 6,207,182 B1
(45) Date of Patent: *Mar. 27, 2001

(54) ADHESIVE PATCH FOR LITHIUM CONTROLLED RELEASE

(75) Inventor: Armando Raimondi, Rome (IT)

(73) Assignees: Istituto Farmacoterapico Italiano, Rome (IT); Unihart Corporation, Dublin (IE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/043,100
(22) PCT Filed: May 30, 1997
(86) PCT No.: PCT/IT97/00124
§ 371 Date: Oct. 21, 1998
§ 102(e) Date: Oct. 21, 1998
(87) PCT Pub. No.: WO97/47291
PCT Pub. Date: Dec. 18, 1997

(30) Foreign Application Priority Data

Jun. 10, 1996 (IT) .............................................. RM96A0409

(51) Int. Cl.⁷ ..................................................... A61F 13/02
(52) U.S. Cl. .......................... 424/448; 424/449; 424/443
(58) Field of Search .................................... 424/443, 448, 424/449, 447

(56) References Cited

U.S. PATENT DOCUMENTS

| | | | |
|---|---|---|---|
| 4,801,458 | * 1/1989 | Hidaka et al. | 424/443 |
| 5,260,066 | * 11/1993 | Wood | 424/447 |
| 5,614,212 | * 3/1997 | D'Angelo | 424/449 |

FOREIGN PATENT DOCUMENTS

| | | |
|---|---|---|
| 849491 | 8/1970 | (CA) . |
| 4242040 | 6/1994 | (DE) . |
| 0602543 | 12/1993 | (EP) . |
| 0528777 | 5/1996 | (EP) . |

OTHER PUBLICATIONS

J. Clinical Pharmacology, vol. 31; 1991; pp. 401–418, XP000602912 by Vasant V. Rande: "Drug Delivery Systems. 6. Transdermal Drug Delivery" (See Abstract, Fig. 3).
Database WPI; Week 9050, Derwent Publications Ltd., London; AN 90–372979, XP002040107 and JP 02 270 818 A (Sekisui Chem. Ind. Co., Ltd.) Nov. 5, 1990; (See Abstract).

* cited by examiner

Primary Examiner—Thurman K. Page
Assistant Examiner—Isis Ghali
(74) Attorney, Agent, or Firm—Baker Botts L.L.P.

(57) ABSTRACT

It is described an adhesive patch for lithium or salts thereof controlled release for transcutaneous adsorption comprising: a thin, flexible, inner support having an inner side and an outer side; an adhesive which is layered onto the support inner side; at least one of lithium salts which is layered onto the support inner side; wherein the support is made of a non-repellent material for the adhesive. Preferred lithium salts are carbonate, sulphate and acetate.

11 Claims, No Drawings

ADHESIVE PATCH FOR LITHIUM CONTROLLED RELEASE

The instant invention concerns an adhesive patch for lithium controlled release.

In particular the invention refers to an adhesive patch for lithium or salts thereof controlled release to be adsorbed transcutaneously, for psychiatric therapy.

Since the XX century the lithium carbonate was used for psychiatric studies; during the last forty years it has widely used in the therapy of psychiatric disorders.

The action mechanism of lithium as mood stabilizer is not completely known. Certainly its activity at level of cell membrane and of the synaptic transmission is of great relevance.

The lithium carbonate is normally taken through oral route by means of tablets or capsules at 0.150 g, two or three times/day, to a total of 1.0–2.0 g per day. Such way of administration has some disadvantages. Firstly, the reoccurrence of administrations is not appreciated by patients. Moreover, drug concentration in the plasma is not steady, due to a discontinuous adsorption thereof. Finally, due to the drug metabolism in the gastrointestinal tract and in the liver, it is necessary to administrate an overdose to get satisfying effects, with poisoning risks and high costs of therapy.

Therefore there is the need of a formulation which lowers lithium dosages, which may be used in a more acceptable way to patients and with more powerful and prolonged pharmacological effects.

The author of the instant invention has set up an adhesive patch for lithium or salts thereof controlled release; exemplificative sales are lithium carbonate, sulphate, acetate, for transcutaneous adsorption, which overcomes the disadvantages of known formulations. In fact, the patch of the intention allows to greatly lower lithium dosages.

The formulated drug is preferably used as mood stabilizer during psychiatric therapies.

It is an object of the invention an adhesive patch for lithium or salts thereof controlled release for a transcutaneous adsorption comprising:

a thin, flexible, inert support having an inner side and an outer side;

an adhesive which is layered onto the support inner side;

at least one of lithium salts which is layered onto the support inner side;

wherein the support is made of a no-repellent is material for the adhesive.

The support is preferably made of polyurethanes.

The adhesive comprises preferably acrylic compounds.

The lithium is preferably present as salts thereof, more preferably carbonate, sulphate and acetate salts, most preferably carbonate salts.

According to a preferred embodiment the lithium salts are mixed with one or more excipients.

Lithium salts are present in amounts comprised between appr. 30 mg/cm$^2$ and appr. 120 mg/cm$^2$ of support surface.

The amount of lithium salts is comprised between appr. 150 mg and appr. 1000 mg/patch.

According to a preferred embodiment the adhesive patch further comprises an inner side protective, removable component, having substantially the same size of the support, preferably with a central pre-cutted rima, more preferably consisting of a paper layer.

It is a further object of the invention the use of at least one of lithium salts as carbonate, sulphate or acetate, for preparing an adhesive patch for lithium or salts thereof controlled release to be adsorbed transcutaneously, for psychiatric therapy.

The invention will be now described for illustrative but not limitative purposes, referring to one way of preparation.

EXAMPLE

An adhesive patch for lithium carbonate, sulphate or acetate controlled release to be adsorbed transcutaneously, was prepared as follows.

On the inner side of a polyurethane plastic support having a 3×3 cm quadrangular shape with rounded angles, a hydroalcoholic solution of lithium carbonate was layered. On the top a layer of acrylic acid adhesive was layered and a paper protective removable layer was added, having a precutted central rima. The patch was allowed to dry.

The invention was described for illustrative but not limitative purposes, according to a preferred embodiment, but it is to be intended that the scope of protection is limited only by the following claims.

What is claimed is:

1. An adhesive patch for providing controlled release of a lithium salt for transcutaneous adsorption comprising:

a thin, flexible, inert support having an inner side and an outer side;

a therapeutically effective amount of at least one lithium salt which is layered directly onto the support inner side; and an adhesive which is layered over the layer containing lithium salt;

wherein the support is made of a material which adheres to the adhesive.

2. The adhesive patch according to claim 1 wherein said support is a polyurethane support.

3. The adhesive patch according to claim 1 wherein said adhesive comprises acrylic compounds.

4. The adhesive patch according to claim 1 wherein said lithium salt is selected from the group comprising carbonate, sulphate and acetate salts.

5. The adhesive patch according to claim 4 wherein said lithium salt is lithium carbonate.

6. The adhesive patch according to claim 1 wherein said lithium salt is mixed with one or more excipients.

7. The adhesive patch according to claim 5 wherein said lithium carbonate is present in an amount between approximately 30 mg/cm$^2$ and approximately 120 mg/cm$^2$ of support surface.

8. The adhesive patch according to claim 7 wherein the amount of lithium salt contained in the patch is between approximately 150 mg and approximately 1000 mg/patch.

9. The adhesive patch according to claim 1, 2, 3, 4, 5, 6, 7 or 8 further comprising an inner side protective, removable component, having substantially the same size of the support.

10. The adhesive patch according to claim 9 wherein said protective component consists of a paper layer.

11. A method of treating a psychiatric disorder comprising administering, transcutaneously, an effective amount of at least one lithium salt, where the salt is selected from the group consisting of a carbonate, sulphate and acetate salt as contained in an adhesive patch according to claim 1.

* * * * *